(12) United States Patent
Chien

(10) Patent No.: US 9,791,721 B2
(45) Date of Patent: Oct. 17, 2017

(54) OPHTHALMIC LENS, INTRAOCULAR LENS, AND LENS MATERIAL

(71) Applicant: HON HAI PRECISION INDUSTRY CO., LTD., New Taipei (TW)

(72) Inventor: Hsiu-Wen Chien, New Taipei (TW)

(73) Assignee: HON HAI PRECISION INDUSTRY CO., LTD., New Taipei (TW)

( * ) Notice: Subject to any disclaimer, the term of this patent is extended or adjusted under 35 U.S.C. 154(b) by 58 days.

(21) Appl. No.: 14/879,837

(22) Filed: Oct. 9, 2015

(65) Prior Publication Data

US 2017/0082871 A1 Mar. 23, 2017

(30) Foreign Application Priority Data

Sep. 18, 2015 (TW) .............................. 104131002 A

(51) Int. Cl.
| | |
|---|---|
| A61F 2/16 | (2006.01) |
| G02C 7/10 | (2006.01) |
| A61L 27/52 | (2006.01) |
| A61L 27/44 | (2006.01) |
| A61L 27/18 | (2006.01) |
| C08K 5/053 | (2006.01) |

(52) U.S. Cl.
CPC ................ *G02C 7/108* (2013.01); *A61F 2/16* (2013.01); *A61L 27/18* (2013.01); *A61L 27/44* (2013.01); *A61L 27/52* (2013.01); *C08K 5/053* (2013.01); *G02C 7/104* (2013.01); *A61F 2002/16965* (2015.04); *A61L 2430/16* (2013.01)

(58) Field of Classification Search
CPC .. A61F 2/16; A61F 2002/16965; G02C 7/104
See application file for complete search history.

(56) References Cited

U.S. PATENT DOCUMENTS

| | | | | |
|---|---|---|---|---|
| 6,180,687 B1 * | 1/2001 | Hammer | ................ | A61K 31/19 424/427 |
| 8,113,651 B2 * | 2/2012 | Blum | ....................... | G02C 7/04 351/159.1 |
| 2002/0111390 A1 * | 8/2002 | Lin | ........................ | C09D 4/06 522/83 |
| 2002/0115756 A1 * | 8/2002 | Lin | ........................ | C09D 4/06 524/100 |

* cited by examiner

*Primary Examiner* — Sanza McClendon
(74) *Attorney, Agent, or Firm* — Steven Reiss

(57) ABSTRACT

An ophthalmic lens includes a matrix and a natural yellow dye dispersed in the matrix. The natural yellow dye includes at least one of lutein and zeaxanthin.

4 Claims, 2 Drawing Sheets

OPHTHALMIC LENS, INTRAOCULAR LENS, AND LENS MATERIAL

FIELD

The subject matter herein generally relates to an ophthalmic lens, an intraocular lens, and a lens material for making the ophthalmic lens and the intraocular lens.

BACKGROUND

For people who are outside, solar radiation is a major factor for harming vision. The sun emits solar radiation including visible rays, ultraviolet (UV) rays, and infrared (IR) rays. The solar radiation is mainly absorbed by the atmosphere. When the remaining solar radiation is transmitted through the atmosphere and reaches the surface, it consists of UV-B rays (230 nm-300 nm), UV and UV-A rays (300 nm-380 nm), visible light rays (380 nm-760 nm), and IR rays (760 nm-1400 nm).

BRIEF DESCRIPTION OF THE DRAWINGS

Implementations of the present technology will now be described, by way of example only, with reference to the attached figures.

DETAILED DESCRIPTION

Figure 1:
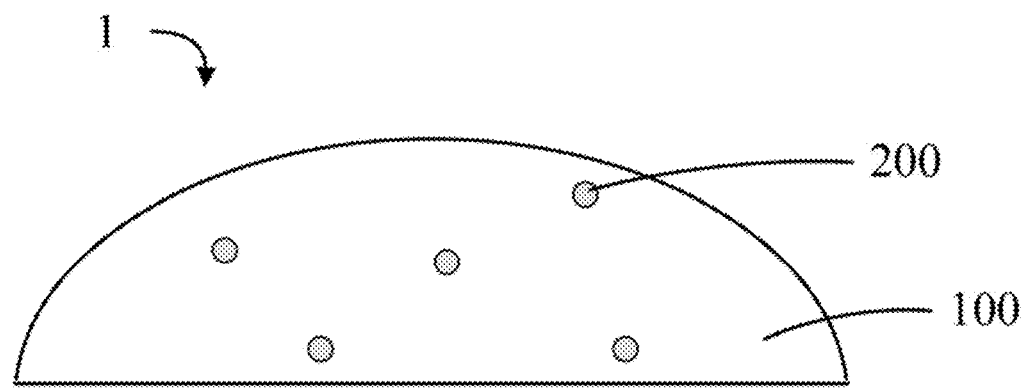
FIG. 1 is a diagrammatic view of an embodiment of an ophthalmic lens according to the present disclosure.

It will be appreciated that for simplicity and clarity of illustration, where appropriate, reference numerals have been repeated among the different figures to indicate corresponding or analogous elements. In addition, numerous specific details are set forth in order to provide a thorough understanding of the embodiments described herein. However, it will be understood by those of ordinary skill in the art that the embodiments described herein can be practiced without these specific details. In other instances, methods, procedures, and components have not been described in detail so as not to obscure the related relevant feature being described. Also, the description is not to be considered as limiting the scope of the embodiments described herein. The drawings are not necessarily to scale and the proportions of certain parts may be exaggerated to better illustrate details and features of the present disclosure.

The term "comprising," when utilized, means "including, but not necessarily limited to"; it specifically indicates open-ended inclusion or membership in the so-described combination, group, series and the like.

FIG. 1 illustrates an embodiment of an ophthalmic lens 1 comprising a matrix 100 and a natural yellow dye 200 dispersed in the matrix 100. The natural yellow dye 200 is able to filter a large portion of blue light with a wavelength of about 450 nm to about 500 nm in an ambient environment and protect the retinal from being damaged by blue light radiation. The natural yellow dye 200 is further able to provide sufficient nutrient for eyes for maintaining healthy eyes.

The natural yellow dye 200 comprises at least one of lutein and zeaxanthin. Lutein and zeaxanthin are two types of carotenoids which can be found in vegetables and other plants. In at least one embodiment, the ophthalmic lens 1 is a contact lens (such as a hydrogel lens or a silicone hydrogel lens).

In at least one embodiment, the natural yellow dye 200 has a mass percentage of about 0.0001% to about 0.5% of a total mass of the ophthalmic lens 1. When the natural yellow dye 200 has a mass percentage of less than 0.0001% of the total mass of the ophthalmic lens 1, the ophthalmic lens 1 may have an unsatisfied ability to filter the blue light. When the natural yellow dye 200 has a mass percentage of greater than 0.5% of the total mass of the ophthalmic lens 1, the ophthalmic lens 1 may have an undesirable yellow appearance, thereby causing objects observed by a user via the ophthalmic lens 1 to be yellower.

In at least one embodiment, the natural yellow dye 200 comprises both lutein and zeaxanthin each having a mass percentage of about 0.00005% to about 0.25% of the total mass of the ophthalmic lens 1.

In at least one embodiment, when the ophthalmic lens 1 is a hydrogel lens, the matrix 100 is hydrogel. When the ophthalmic lens 1 is a silicone hydrogel lens, the matrix 100 is silicone hydrogel. The hydrogel and the silicone hydrogel are formed by hydrophilic monomers and hydrated polymers which undergo a polymerization reaction under the function of a photoinitiator and a cross-linking agent. The hydrated polymers function as backbones of the hydrogel and the silicone hydrogel. The hydrophilic monomers are bonded to the hydrated polymers to improve hydrophilicity and oxygen permeability of the hydrogel and the silicone hydrogel.

When the matrix 100 is hydrogel, the hydrophilic monomers may be selected from a group consisting of N-vinyl pyrrolidone (NVP), glycidyl methacrylate (GMA), and N,N-dimethylacrylamide (DMA), or any combination thereof. The hydrated polymers may comprise methyl methacrylate (MMA) and 2-hydroxyethyl methacrylate (HEMA). When the matrix 100 is silicone hydrogel, the hydrophilic monomers may be N-vinyl pyrrolidone (NVP). The hydrated polymers may be selected from a group consisting of methyl methacrylate (MMA), 2-hydroxyethyl methacrylate (HEMA), polydimethylsiloxane (PDMS), and (hydroxymethyl)aminomethane (TRIS).

The photoinitiator may be available commercially from Chemical Industries Basel (CIBA) Corporation as a clear liquid under the trade name "Irgacure-1173". The cross-linking agent may be ethyleneglycol dimethacrylate (EGDMA).

EXAMPLE 1

The ophthalmic lens 1 comprises hydrogel and lutein dispersed in the hydrogel. The luteina has a mass percentage of 0.4% of the total mass of the ophthalmic lens 1.

EXAMPLE 2

The ophthalmic lens 1 comprises hydrogel, and lutein and zeaxanthin dispersed in the hydrogel. Each of the luteina and the zeaxanthin has a mass percentage of 0.2% of the total mass of the ophthalmic lens 1.

EXAMPLE 3

The ophthalmic lens 1 comprises silicone hydrogel, and lutein and zeaxanthin dispersed in the hydrogel. Each of the luteina and the zeaxanthin has a mass percentage of 0.15% of the total mass of the ophthalmic lens 1.

Figure 2:
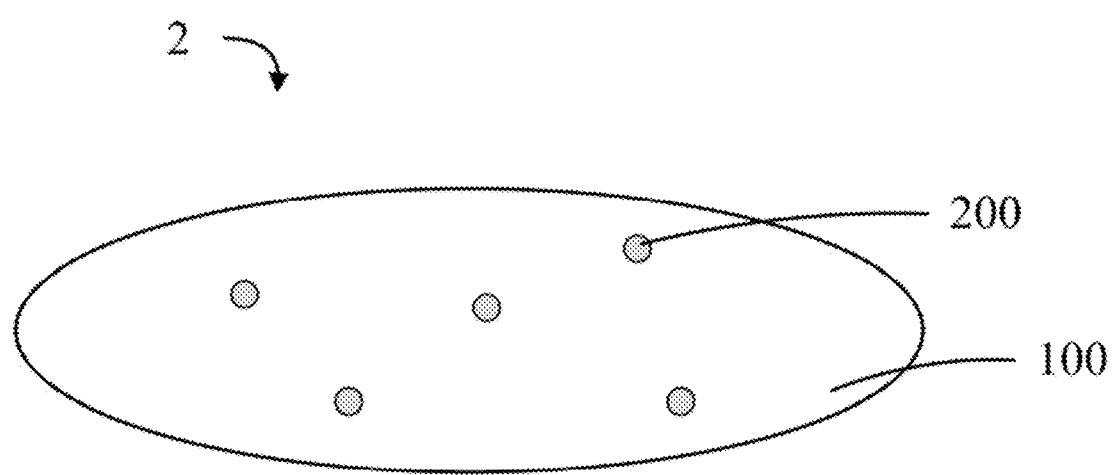
FIG. 2 is a diagrammatic view of an embodiment of an intraocular lens according to the present disclosure.

FIG. 2 illustrates an embodiment of an intraocular lens 2 also comprising the matrix 100 and the natural yellow dye 200 dispersed in the matrix 100. The natural yellow dye 200 comprises at least one of lutein and zeaxanthin.

A lens material for making the ophthalmic lens 1 or the intraocular lens 2 is provided according the present disclosure. The lens material comprises natural yellow dye 200, hydrophilic monomers, hydrated polymers, a photoinitiator, and a cross-linking agent. When exposed to light, the hydrophilic monomers and hydrated polymers undergo a polymerization reaction under the function of the photoinitiator and the cross-linking agent to form the matrix 100, thereby causing the natural yellow dye 200 to be dispersed in the matrix 100. The natural yellow dye 200 comprises at least one of lutein and zeaxanthin.

It is to be understood, even though information and advantages of the present embodiments have been set forth in the foregoing description, together with details of the structures and functions of the present embodiments, the disclosure is illustrative only; changes may be made in detail, especially in matters of shape, size, and arrangement of parts within the principles of the present embodiments to the full extent indicated by the plain meaning of the terms in which the appended claims are expressed.

What is claimed is:

1. An ophthalmic lens comprising:
   a matrix; and
   a natural yellow dye dispersed in the matrix;
   wherein the natural yellow dye comprises both lutein and zeaxanthin each having a mass percentage of about 0.00005% to about 0.25% of a total mass of the ophthalmic lens.

2. The ophthalmic lens of claim 1, wherein the matrix is hydrogel or silicone hydrogel.

3. An intraocular lens comprising:
   a matrix; and
   a natural yellow dye dispersed in the matrix;
   wherein the natural yellow dye comprises both lutein and zeaxanthin each having a mass percentage of about 0.00005% to about 0.25% of a total mass of the ophthalmic lens.

4. The intraocular lens of claim 3, wherein the matrix is hydrogel or silicone hydrogel.

* * * * *